(12) United States Patent
Brisson et al.

(10) Patent No.: US 11,684,381 B2
(45) Date of Patent: *Jun. 27, 2023

(54) SURGICAL INSTRUMENT WITH SINGLE DRIVE INPUT FOR TWO END EFFECTOR MECHANISMS

(71) Applicant: Intuitive Surgical Operations, Inc., Sunnyvale, CA (US)

(72) Inventors: Gabriel F. Brisson, Albany, CA (US); Alan E. Loh, Los Altos, CA (US); Lawrence Kerver, Los Gatos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 712 days.

This patent is subject to a terminal disclaimer.

(21) Appl. No.: 16/836,292

(22) Filed: Mar. 31, 2020

(65) Prior Publication Data

US 2020/0289142 A1 Sep. 17, 2020

Related U.S. Application Data

(60) Continuation of application No. 15/669,100, filed on Aug. 4, 2017, now Pat. No. 10,639,055, which is a (Continued)

(51) Int. Cl.
*A61B 17/295* (2006.01)
*A61B 34/30* (2016.01)
(Continued)

(52) U.S. Cl.
CPC .......... *A61B 17/295* (2013.01); *A61B 17/285* (2013.01); *A61B 17/320016* (2013.01);
(Continued)

(58) Field of Classification Search
CPC . A61B 17/128; A61B 17/1285; A61B 17/285; A61B 17/295; A61B 17/28;
(Continued)

(56) References Cited

U.S. PATENT DOCUMENTS 4,815,460 A   3/1989 Porat et al.
5,015,252 A   5/1991 Jones
(Continued)

OTHER PUBLICATIONS

International Search Report and Written Opinion for Application No. PCT/US2012/040037, dated Jan. 10, 2013, 14 pages.
(Continued)

*Primary Examiner* — Wade Miles
(74) *Attorney, Agent, or Firm* — Kilpatrick Townsend & Stockton LLP

(57) ABSTRACT

Methods for treating tissue, and surgical assemblies and related methods are disclosed in which a single input is used to sequentially articulate two members. A medical device includes an input link movable through an input link range of motion, a jaw coupled with the input link, and a tissue manipulation member coupled to the input link and positioned to manipulate a tissue gripped by the jaw. The input link range of motion includes a first portion and a second portion. The input link within the first portion of the input link range of motion drives the jaw through a jaw range of motion. The input link within the second portion of the input link range of motion drives the tissue manipulation member through a tissue manipulation member range of motion.

20 Claims, 10 Drawing Sheets

Related U.S. Application Data continuation of application No. 14/498,750, filed on Sep. 26, 2014, now Pat. No. 9,730,719, which is a division of application No. 13/484,143, filed on May 30, 2012, now Pat. No. 8,870,912.

(60) Provisional application No. 61/491,821, filed on May 31, 2011.

(51) Int. Cl.
*A61B 17/32* (2006.01)
*A61B 17/285* (2006.01)
*A61B 17/00* (2006.01)
*A61B 17/29* (2006.01)
*A61B 18/14* (2006.01)

(52) U.S. Cl.
CPC .... *A61B 34/30* (2016.02); *A61B 2017/00389* (2013.01); *A61B 2017/2915* (2013.01); *A61B 2017/2936* (2013.01); *A61B 2018/1455* (2013.01)

(58) Field of Classification Search
CPC . A61B 17/2812; A61B 17/29; A61B 17/2926; A61B 17/320016; A61B 17/320036; A61B 2017/32004; A61B 2017/2927
See application file for complete search history.

(56) References Cited

U.S. PATENT DOCUMENTS

| | | |
|---|---|---|
| 5,254,129 A | 10/1993 | Alexander |
| 5,281,230 A | 1/1994 | Heidmueller |
| 5,383,880 A | 1/1995 | Hooven |
| 5,423,854 A | 6/1995 | Martin et al. |
| 5,752,973 A | 5/1998 | Kieturakis et al. |
| 5,976,161 A | 11/1999 | Kirsch et al. |
| 7,682,372 B2 | 3/2010 | Peterson |
| 7,918,230 B2 | 4/2011 | Whitman et al. |
| 8,430,877 B2 | 4/2013 | Kerr et al. |
| 8,491,624 B2 | 7/2013 | Kerr et al. |
| 8,496,682 B2 | 7/2013 | Guerra et al. |
| 8,870,912 B2 | 10/2014 | Brisson et al. |
| 9,730,719 B2 | 8/2017 | Brisson et al. |
| 10,639,055 B2 * | 5/2020 | Brisson .......... A61B 17/320016 |
| 2005/0021079 A1 | 1/2005 | Kalmann et al. |
| 2007/0043352 A1 | 2/2007 | Garrison et al. |
| 2013/0023911 A1 * | 1/2013 | Esanu ................ A61B 17/29 606/151 |
| 2013/0190732 A1 * | 7/2013 | Slisz ................ A61B 17/1285 606/1 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

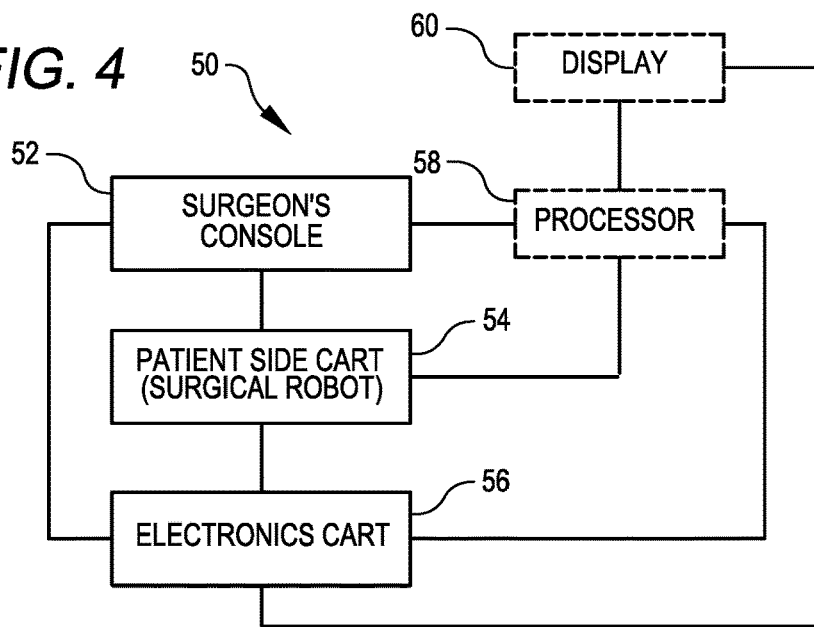
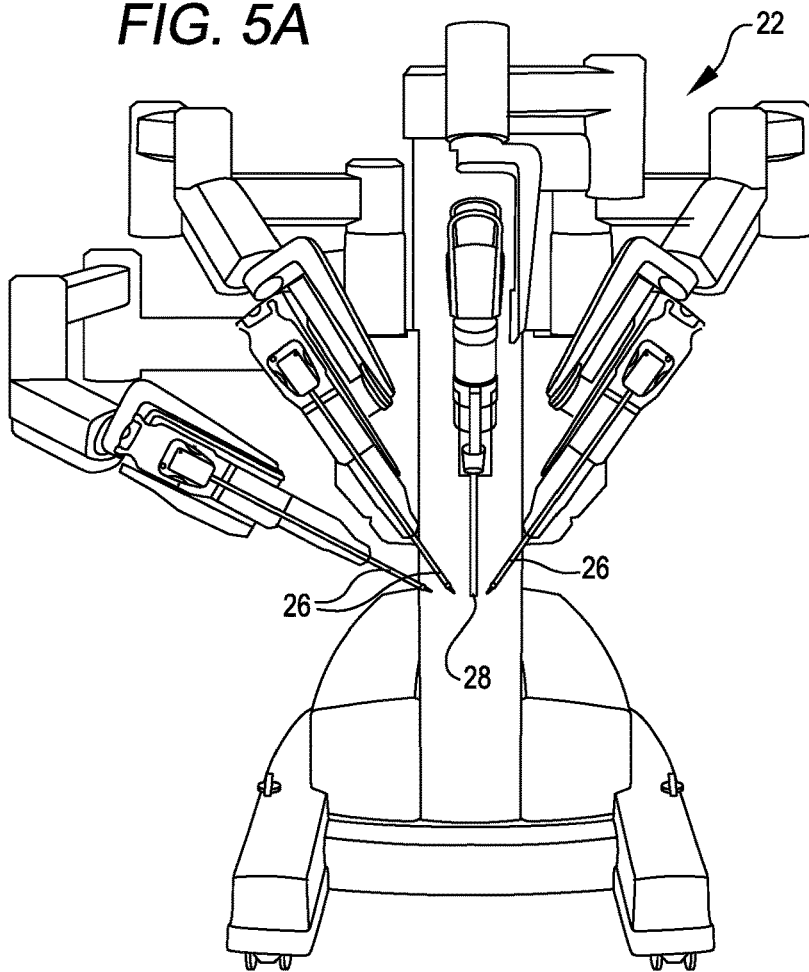

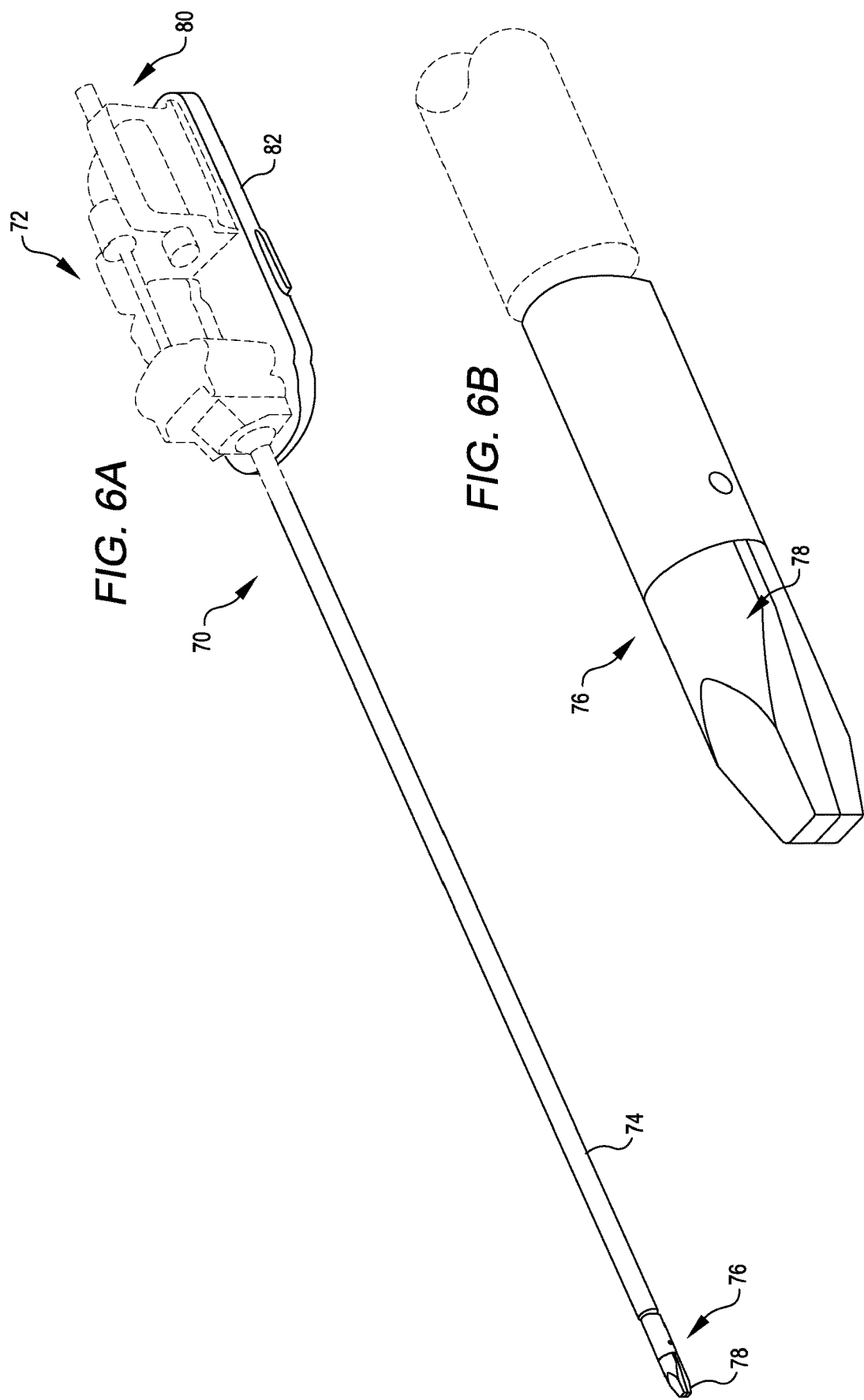

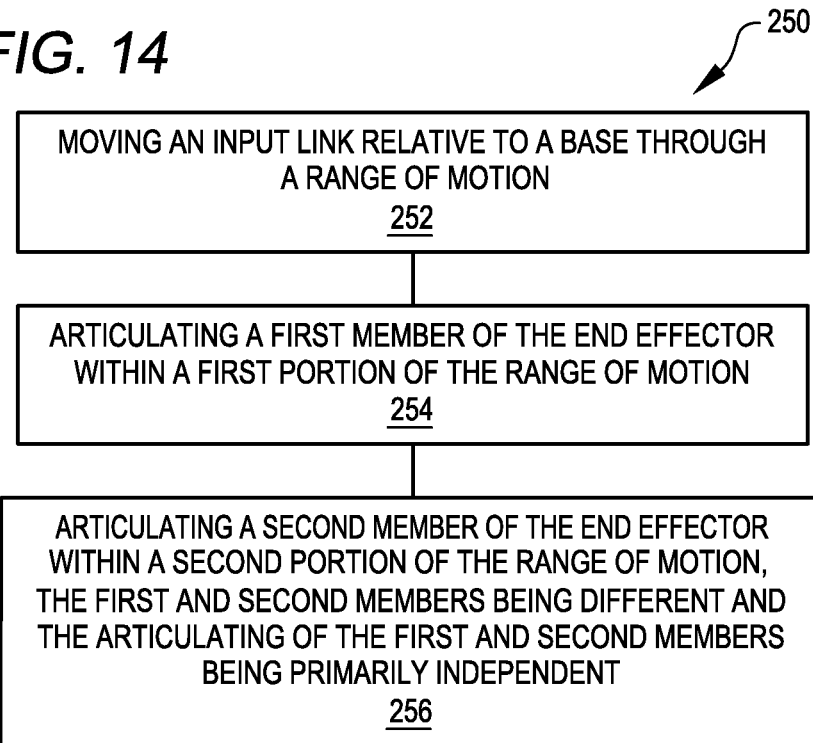
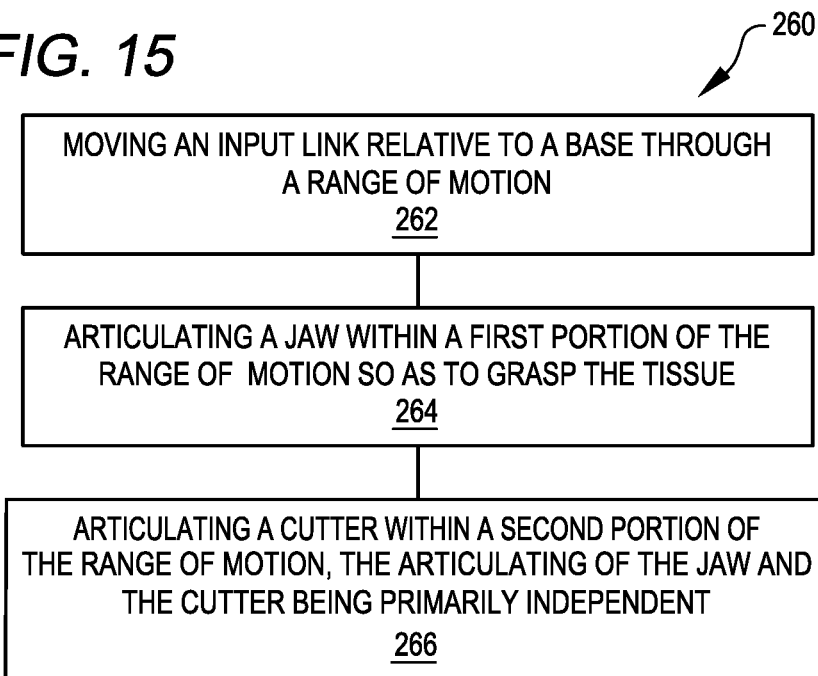

SURGICAL INSTRUMENT WITH SINGLE DRIVE INPUT FOR TWO END EFFECTOR MECHANISMS

CROSS-REFERENCES TO RELATED APPLICATIONS

This application is a Continuation of U.S. Ser. No. 15/669,100 filed Aug. 4, 2017 (Allowed); which is a Continuation of U.S. Ser. No. 14/498,750 filed Sep. 26, 2014 (now U.S. Pat. No. 9,730,719); which is a Divisional of U.S. Ser. No. 13/484,143 filed May 30, 2012 (now U.S. Pat. No. 8,870,912); which claims the benefit of U.S. Provisional Application No. 61/491,821 filed May 31, 2011; the disclosures which are incorporated herein by reference in their entirety for all purposes.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices.

Manipulation and control of these end effectors is a particularly beneficial aspect of robotic surgical systems. For this reason, it is desirable to provide surgical tools that include mechanisms that provide three degrees of rotational movement of an end effector to mimic the natural action of a surgeon's wrist. Such mechanisms should be appropriately sized for use in a minimally invasive procedure and relatively simple in design to reduce possible points of failure. In addition, such mechanisms should provide an adequate range of motion to allow the end effector to be manipulated in a wide variety of positions.

Non-robotic linear clamping, cutting and stapling devices have been employed in many different surgical procedures. For example, such a device can be used to resect a cancerous or anomalous tissue from a gastro-intestinal tract. Many known surgical devices, including known linear clamping, cutting and stapling devices, often have opposing jaws that are used to manipulate patient tissue.

In many existing minimally invasive telesurgical robotic systems, manipulation of the surgical instruments is provided by a surgical robot having a number of robotic arms. Each of the robotic arms has a number of robotic joints and a mounting fixture for the attachment of a surgical instrument. Integrated in with at least one of the mounting fixtures are a number of drive couplers (e.g., rotary drive couplers) that drivingly interface with corresponding input couplers of the surgical instrument. The surgical instrument includes mechanisms that drivingly couple the input couplers with an associated motion of the surgical instrument (e.g., main shaft rotation, end effector pitch, end effector yaw, end effector jaw clamping). In many existing minimally invasive telesurgical robotic systems, there are four drive couplers integrated in with each of the mounting fixtures (e.g., one drive coupler to actuate main shaft rotation, one drive coupler to actuate end effector pitch, one drive coupler to actuate end effector yaw, and one drive coupler to actuate end effector jaw articulation).

A problem arises, however, when it is desired to employ a surgical robot having a number of output couplers per mounting fixture (e.g., four) to manipulate a surgical instrument having more than that number of functions (e.g., five such as main shaft rotation, end effector pitch, end effector yaw, end effector jaw clamping, and tissue cutting).

Thus, there is believed to be a need for surgical assemblies and related methods that employ a single input drive for two end effector functions (e.g., two different mechanisms).

BRIEF SUMMARY

Methods for treating tissue, and surgical assemblies and related methods are disclosed in which a single input is used to sequentially articulate two members. The single input is moved through a range of motion. During a first portion of the range of motion, the input link is drivingly coupled with a first articulated member (e.g., a jaw operable to grip tissue). Then, during a second portion of the range of motion, the input link is drivingly coupled with a second articulated member (e.g., a cutter operable to cut tissue). Accordingly, a robotic arm having a number of output couplers per mounting fixture (e.g., four) can be used to manipulate a surgical instrument having more than that number of functions (e.g., five such as main shaft rotation, end effector pitch, end effector yaw, end effector jaw clamping, and tissue cutting).

Thus, in a first aspect, a surgical assembly is provided. The surgical assembly includes an end effector, a base supporting the end effector, an input link movable relative to the base through a range of motion between a first configuration and a second configuration, and an actuation mechanism. The end effector includes a first articulated member and a second articulated member. The actuation mechanism drivingly couples the input link to the first articulated member within a first portion of the range of motion and drivingly coupling the input link with the second articulated member within a second portion of the range of motion so that a movement of the input link from the first configuration to the second configuration articulates the first articulated member and then articulates the second articulated member.

In many embodiments of the surgical assembly, the first and second articulated members are configured to manipulate tissue. For example, the first articulated member can have a first articulation range configured for a first desired manipulation of tissue. And the second articulated member can have a second articulation range configured for a second desired manipulation of tissue. The movement of the input link can actuate the first articulated member throughout the first articulation range primarily within the first portion of the range of motion, and can actuate the second articulated member throughout the second articulation range within the second portion of the range of motion. The first and second portions of the range of motion are separate so as to facilitate independently effecting the first and second desired manipulations of tissue. In many embodiments, the first articulated member includes a jaw operable to grip tissue and the second articulated member includes a cutter operable to cut tissue.

In many embodiments of the surgical assembly, the input link is drivingly coupled with the jaw through a spring that deflects during the second portion of the range of motion to at least partially decouple motion of the jaw from motion of the input link during the second portion of the range of motion. For example, the spring can inhibit relative movement between the input link and a first output link during the first portion of the range of motion, the first output link being drivingly coupled with the jaw. The spring can deflect to allow relative motion between the input link and the first output link during the second portion of the range of motion. And the input link can drive a second output link during the second portion of the range of motion, the second output link being drivingly coupled with the cutter.

Any suitable type of spring can be used. For example, the spring can include an extension spring. And linear motion of the input link relative to the base can be used to induce articulation of the jaw and the cutter. As another example, the spring can include a torsion spring. And rotation of the input link relative to the base can be used to induce articulation of the jaw and the cutter.

The actuation mechanism can include a cam surface drivingly coupled with the input link and shaped to inhibit driving of the cutter during the first portion of the range of motion and drive the cutter during the second portion of the range of motion. For example, a rotation of the input link relative to the base can be used to induce a rotation of the cam surface relative to the base. The actuation mechanism can include a member with a slot that defines the cam surface and a follower that engages the slot and is drivingly coupled with the cutter by a linkage. The slotted member can be mounted for rotation relative to the base about an axis of rotation. The slot can include a first segment having a centerline with a constant radius relative to the axis of rotation and a second segment having a centerline with a varying radius relative to the axis of rotation. The follower can engage the first segment during the first portion of the range of motion and can engage the second segment during the second portion of the range of motion.

The actuation mechanism can include two separate cam surfaces that are drivingly coupled with the input link. For example, a first cam surface can be drivingly coupled with the input link and shaped to actuate the first articulated member. And a second cam surface can also be coupled with the input link and shaped to actuate the second articulated member. The first cam surface can be part of a first slotted member that is drivingly coupled with the input link. And the second cam surface can be part of a second slotted member that is drivingly coupled with the input link. The first and second articulated members can be drivingly coupled with respective followers that engage the first and second cam surfaces, respectively.

The actuation mechanism can include one or more cam surfaces such as disclosed herein and the input link can be drivingly coupled with the jaw through a spring that deflects to at least partially decouple motion of the jaw from motion of the input link such as disclosed herein. Such a combined embodiment can be used to provide flexibility with regard to the amount of jaw articulation that occurs prior to the articulation of the cutter, such as when items of different sizes are gripped by the jaw.

In another aspect, a method of treating tissue is provided. The method includes moving an input link relative to a base through a range of motion, articulating a jaw within a first portion of the range of motion so as to grasp the tissue, and articulating a cutter within a second portion of the range of motion so as to cut the tissue, the articulating of the jaw and the cutter being primarily independent.

In many embodiments of the method of treating tissue, the articulation of the jaw includes inhibiting relative movement between the input link and an output link during the first portion of the range of motion with a spring coupled with the input link and the output link, the output link being drivingly coupled with the jaw. The articulation of the cutter can include deflecting the spring to at least partially decouple motion of the output link from the input link during the second portion of the range of motion.

Any suitable type of spring can be used. For example, the spring can include an extension spring. And the method can include translating the input link relative to the base to induce the articulation of the jaw and the cutter. As another example, the spring can include a torsion spring. And the method can include rotating the input link relative to the base to induce the articulation of the jaw and the cutter.

In many embodiments, the method of treating tissue includes rotating a member having a slot in response to rotation of the input link and engaging the slot with a follower that is drivingly coupled with the cutter. The method of treating tissue can include rotating the slotted member about an axis of rotation relative to the base. The slot can include a first segment having a centerline with a constant radius relative to the axis of rotation and a second segment having a centerline with a varying radius relative to the axis of rotation. The method of treating tissue can include engaging the first segment with the follower during the first portion of the range of motion and engaging the second segment with the follower during the second portion of the range of motion.

The method of treating tissue can include both rotating a member having a slot in response to rotation of the input link and engaging the slot with a follower that is drivingly coupled with the cutter such as disclosed herein, and inhibiting relative movement between the input link and an output link with a spring coupled with the input link and the output link, the output link being drivingly coupled with the jaw, such as disclosed herein. And the method can include deflecting the spring to at least partially decouple motion of the output link from the input link such as disclosed herein. Such a combined embodiment can be used to provide flexibility with regard to the amount of jaw articulation that occurs prior to the articulation of the cutter, such as when items of different sizes are gripped by the jaw.

In another aspect, a method is provided for articulating an end effector of a surgical assembly. The method includes moving an input link relative to a base through a range of motion, articulating a first member of the end effector within a first portion of the range of motion, and articulating a second member of the end effector within a second portion of the range of motion, the first and second members being different and the articulating of the first and second members being primarily independent.

In many embodiments of the method for articulating an end effector of a surgical assembly, the first member includes a jaw configured to grip a tissue and the second member includes a cutter configured to cut the tissue. In many embodiments of the method for articulating an end effector of a surgical assembly, the jaw has a first articulation range configured to grip a tissue and the cutter has a second articulation range configured to cut the tissue. Movement of the input link actuates the jaw throughout the first articulation range primarily within the first portion of the range of motion, and actuates the cutter throughout the second articulation range within the second portion of the range of motion. The first and second portions of the range of motion are separate so as to facilitate independently gripping the tissue and cutting the gripped tissue.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 4 diagrammatically illustrates a robotic surgery system, in accordance with many embodiments.

FIG. 5A is a front view of a patient side cart (surgical robot) of a robotic surgery system, in accordance with many embodiments.

FIG. 6A is a perspective view of a robotic surgery tool that includes an end effector having opposing clamping jaws, in accordance with many embodiments.

FIG. 6B is a close-up perspective view of the end effector of FIG. 6A.

FIG. 14 illustrates acts of a method for articulating two separate members of an end effector by using a single input, in accordance with many embodiments.

FIG. 15 illustrates acts of a method for treating tissue, in accordance with many embodiments.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Minimally Invasive Robotic Surgery

Figure 1:
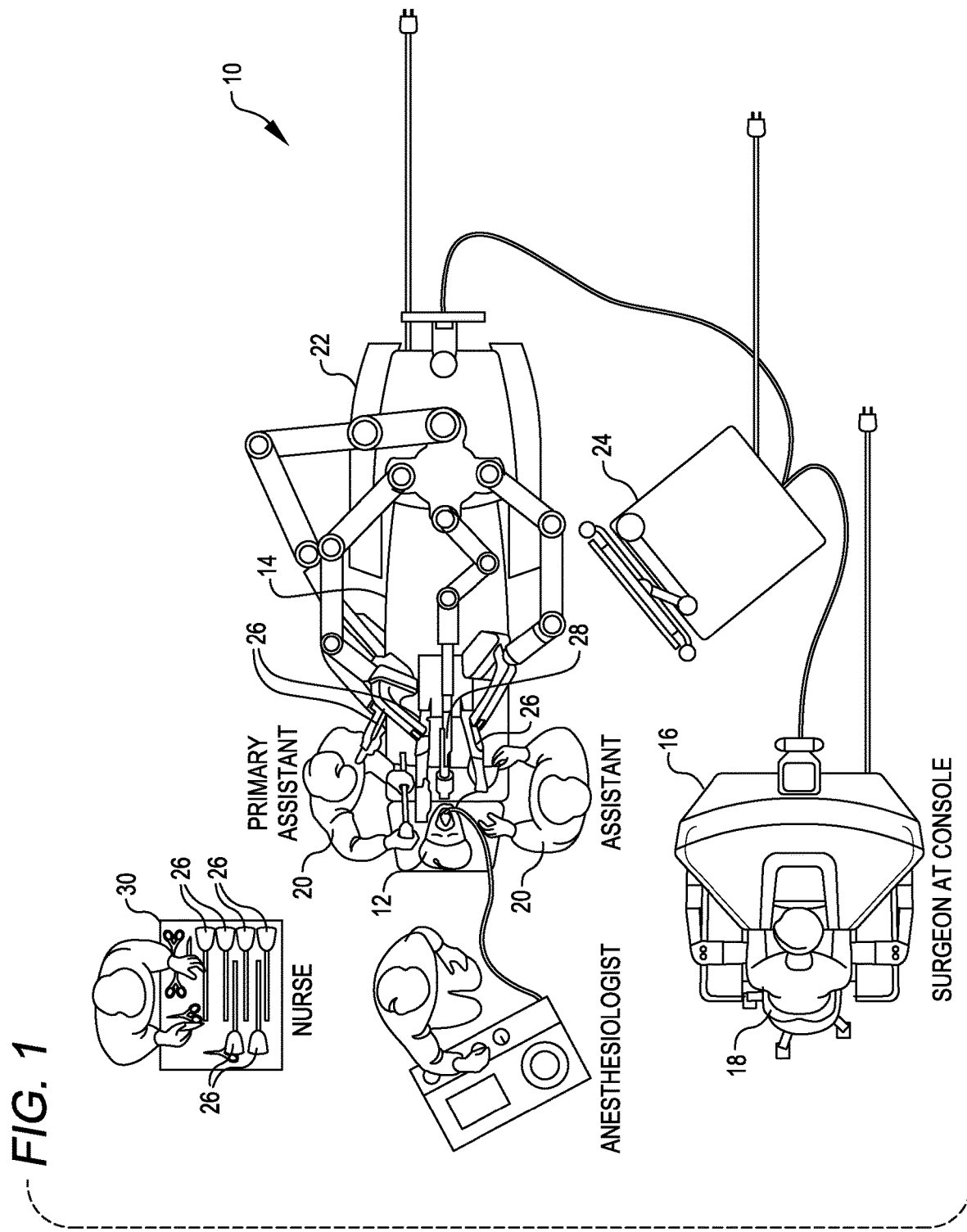
FIG. 1 is a plan view of a minimally invasive robotic surgery system being used to perform a surgery, in accordance with many embodiments.

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 so as to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
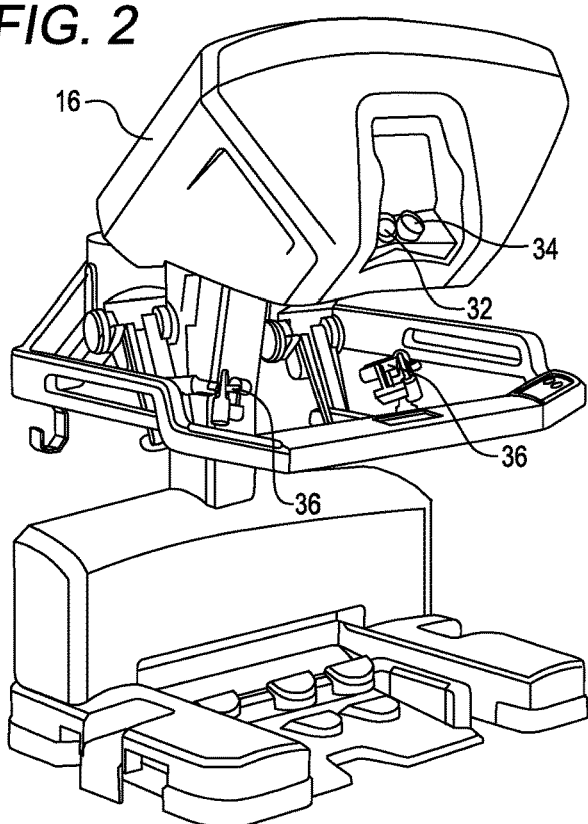
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) so as to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
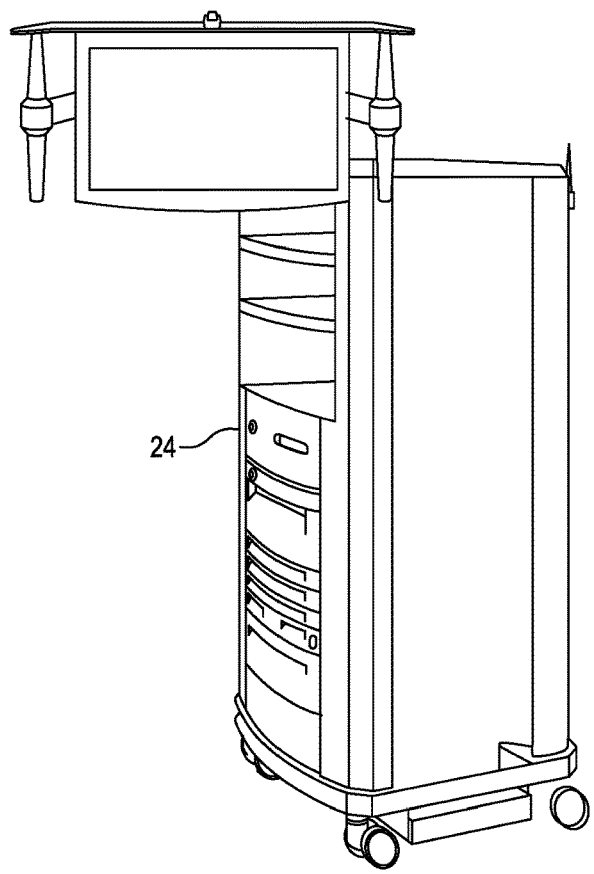
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images so as to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together so as to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5B:
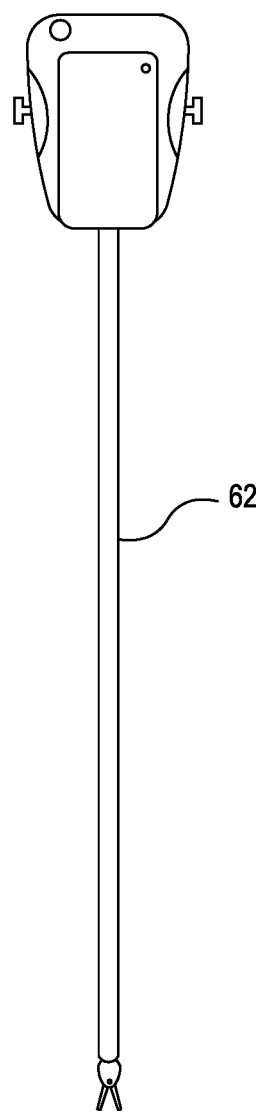
FIG. 5B is a front view of a robotic surgery tool, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical tools 26 when they are positioned within the field-of-view of the imaging device 28.

Tissue Gripping End Effectors

FIG. 6A shows a surgical tool 70 that includes a proximal chassis 72, an instrument shaft 74, and a distal end effector 76 having a jaw 78 that can be articulated to grip a patient tissue. The proximal chassis includes an input coupler that is configured to interface with and be driven by an output coupler of the Patient Side Cart 22. The input coupler is drivingly coupled with an input link of a spring assembly 80. The spring assembly 80 is mounted to a frame 82 of the proximal chassis 72 and includes an output link that is drivingly coupled with a drive shaft that is disposed within the instrument shaft 74. The drive shaft is drivingly coupled with the jaw 78. FIG. 6B provides a close-up view of the jaw 78 of the end effector 76.

Figure 7:
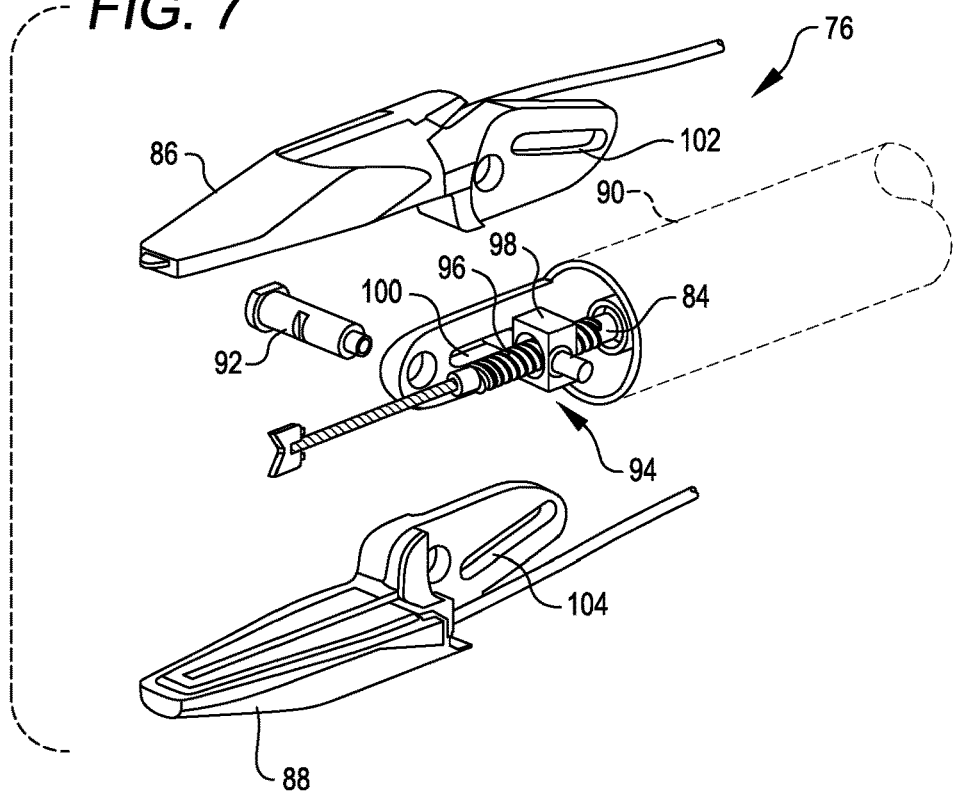
FIG. 7 is an exploded perspective view of the end effector of FIG. 6A, illustrating a mechanism used to convert rotary motion of a drive shaft into articulation of the opposing clamping jaws.

FIG. 7 is an exploded perspective view of the end effector 76 of FIG. 6A, illustrating a clamping mechanism used to convert rotary motion of a drive shaft 84 into articulation of opposing clamping jaws of the end effector 76. The end effector includes an upper jaw 86, a lower jaw 88, a frame 90, a pin 92 for pivotally mounting the upper jaw 86 and the lower jaw 88 to the frame 90, and a lead screw mechanism 94 that is drivingly coupled with the drive shaft 84. The lead screw mechanism 94 includes a lead screw 96 and a mating translating nut 98 that is advanced and retracted along a slot 100 in the frame 90 via rotation of the lead screw 96. The translating nut 98 includes oppositely extending protrusions that interface with a slot 102 in the upper jaw 86 and with a slot 104 in the lower jaw 88, thereby causing articulation of the upper jaw 86 and the lower jaw 88 about the pin 92 when the translating nut 98 is advanced or retracted along the slot 100.

The end effector 76 further includes a cutter 106 operable to cut a gripped tissue. The cutter 106 is coupled to a drive member 108. The cutter 106 is advanced distally by a corresponding distal advancement of the drive member 108 and is retracted proximally by a corresponding proximal retraction of the drive member 108. Each of the upper jaw 86 and the lower jaw 88 include a slot 110 that can accommodate a portion of the cutter 106 throughout its range of travel, thereby serving to restrain and guide the cutter 106 throughout its range of motion. In many embodiments, the drive member 108 extends between the cutter 106 and the proximal chassis 72 and is drivingly coupled with an actuation mechanism disposed in the proximal chassis. The actuation mechanism in the proximal chassis can push the drive member 108 distally to advance the cutter 106 distally to cut a gripped tissue. The actuation mechanism can pull the drive member 108 proximally to return the cutter 106 to a retracted starting position.

Figure 8A:
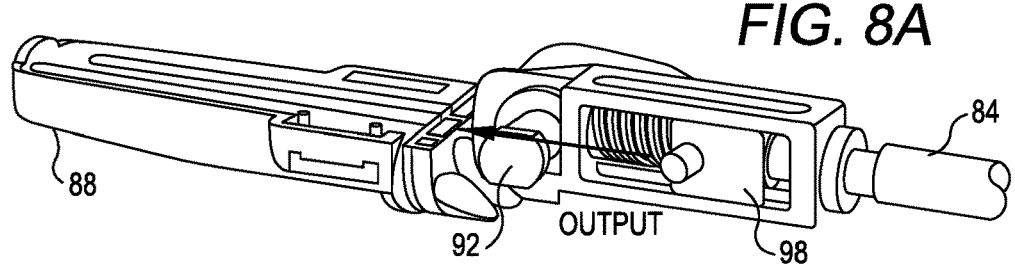
FIGS. 8A and 8B are perspective views of an end effector having opposing clamping jaws and a mechanism used to convert rotary motion of a drive shaft into articulation of the opposing clamping jaws, in accordance with many embodiments.
Figure 8B:
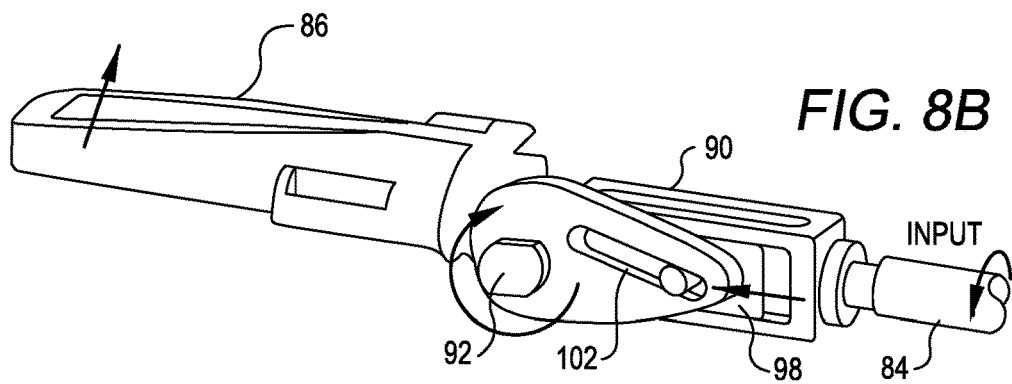

FIG. 8A and FIG. 8B illustrate the operation of a clamping mechanism similar to the clamping mechanism of FIG. 7. Rotating the drive shaft 84 in the direction shown causes a translating nut 98 to advance distally toward the pivot pin 92 by which the lower jaw 88 and the upper jaw 86 are pivotally mounted to the frame 90 of an end effector. As illustrated in FIG. 8B, a protrusion of the translating nut 98 engages the slot 102 in the upper jaw 86. Distal advancement of the translating nut 98 toward the pivot pin 92 causes the upper jaw to rotate in the direction shown, and causes the lower jaw 88 to rotate in the opposite direction, thereby opening the jaw. Similarly, proximal advancement of the translating nut 98 away from the pivot pin 92 cause the jaw to close. Accordingly, the jaw can be articulated to grip a patient tissue.

The end effector 76 can be used to sequentially grip a tissue and then cut the gripped tissue. For example, with the cutter 106 positioned at the retracted starting position (i.e., positioned proximal to the gripping surfaces of the jaw), the jaw 78 can be articulated to grip a tissue. Then, proximal advancement of the cutter 106 along the slots 110 can be accomplished to cut the gripped tissue.

Single Drive Input for Two End Effector Mechanisms

Figure 9:
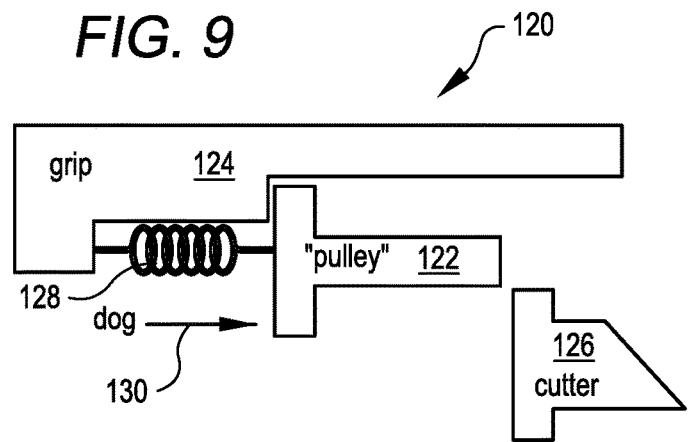
FIG. 9 is a simplified schematic illustrating an actuation mechanism in which a single input link is used to sequentially articulate two members, in accordance with many embodiments.

FIG. 9 schematically illustrates an actuation mechanism 120 in which a single input link 122 is used to sequentially articulate two members, in accordance with many embodiments. The actuation mechanism 120 includes the input link 122, a first output link 124 that is drivingly coupled with the jaw 78 operable to grip tissue, a second output link 126 that is drivingly coupled with the cutter 106 operable to cut the gripped tissue, and a preloaded spring 128 coupled between the input link 122 and the first output link 124. An input coupler 130 (also known as an input "dog") is drivingly coupled with the input link 122.

The input link 122 is driven by the input coupler 130 through a range of motion (e.g., from left to right in FIG. 9). During a first portion of the range of motion, the preloaded spring 128 pulls the first output link 124 to the right, and thereby maintaining contact between the input link 122 and the first output link 124. At some point during the range of motion, the jaw begins to either grip tissue or reaches a closed configuration, thereby causing the actuation force transferred to the jaw by the first output link 124 to increase. Once the actuation force transferred to the jaw by the first output link 124 exceeds a predetermined level corresponding to the preload force level in the preloaded spring 128, further movement of the input link 122 to the right causes the preloaded spring 128 to extend, thereby allowing the input link 122 and the first output link 124 to separate. Further movement of the input link 122 to the right causes further extension of the preloaded spring 128, thereby causing increased separation between the input link 122 and the first output link 124.

During a second portion of the range of motion (i.e., after the first portion of the range of motion), the input link 122 comes into contact with the second output link 126, which is drivingly coupled with the cutter 106. Further movement of the input link 122 to the right drives the second output link 126 to the right, thereby causing actuation of the cutter 106. During the second portion of the range of motion, extension of the preloaded spring 128 provides for an increasing amount of separation between a substantially non-moving first output link 124 and the input link 122 as the input link 122 drives the second output link 126 to the right. The second output link 126 and/or the cutter 106 can be attached to a return mechanism (e.g., a spring) that returns the second output link 126 and/or the cutter 106 to the retracted starting position in the absence of contact between the input link 122 and the second output link 126 (e.g., during the first portion of the range of motion of the input link).

While the actuation mechanism 120 is shown and described with respect to the preloaded spring 128 being an extension spring, any suitable spring can be used. For example, the preloaded spring 128 can be a torsion spring and rotational movement of the input coupler 130 can induce rotational movement of the input link 122, rotational driving of the first output link 124, rotational deflection of the preloaded torsion spring 128, and rotational driving of the second output link 126.

Figure 10:
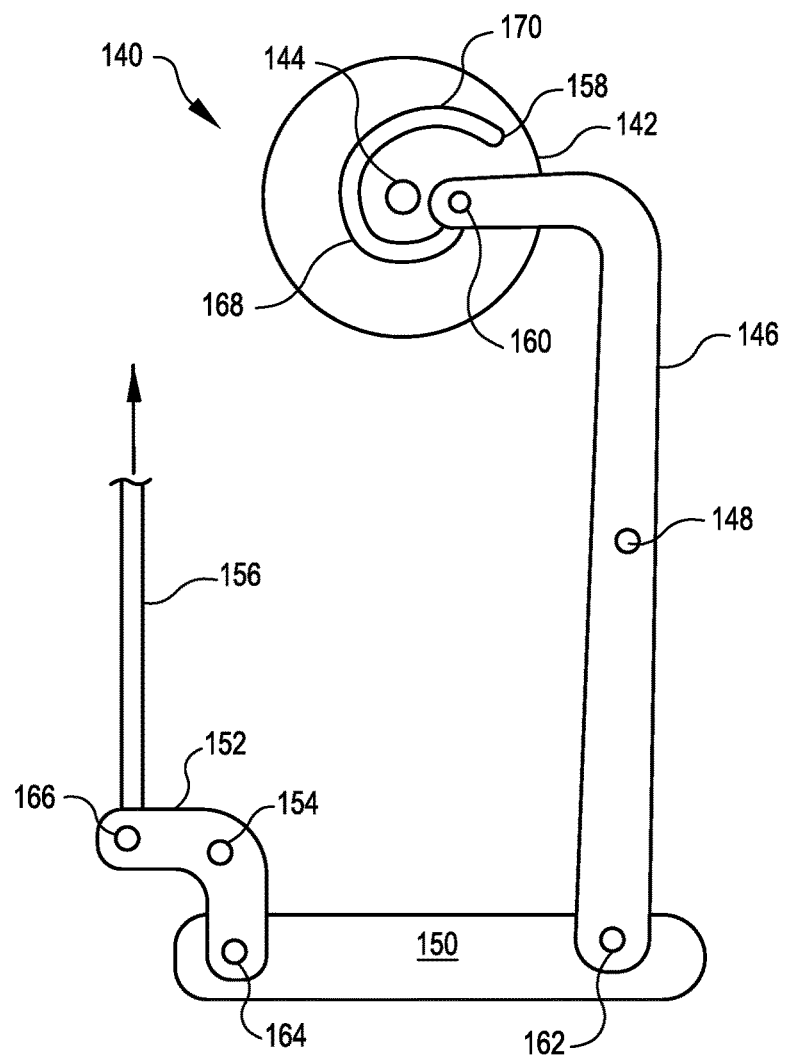
FIG. 10 is a simplified schematic illustrating a mechanism that actuates a cutter during a second portion of a range of rotational motion of an input link, in accordance with many embodiments.

FIG. 10 schematically illustrates another actuation mechanism 140 in which a single input link 142 is used to sequentially articulate two members, in accordance with many embodiments. The actuation mechanism 140 includes the input link 142 mounted for rotation relative to a base around a rotation axis 144, a first toggle link 146 mounted for rotation relative to the base around a first pivot point 148, a connection link 150, a second toggle link 152 mounted for rotation relative to the base around a second pivot point 154, and a drive link 156. The input link 142 includes a slot 158. The first toggle link 146 includes a follower 160 that engages the slot 158. The first toggle link 146 is coupled with the connection link 150 via a first connection pin 162. The connection link 150 is coupled with the second toggle link 152 via a second connection pin 164. The second toggle link 152 is coupled with the drive link 156 via a third connection pin 166.

The input link 142 and the output link 156 are used to sequentially articulate the two members. The input link 142 is drivingly coupled with an actuation mechanism that articulates a first of the two members. For example, the input link 142 can be drivingly coupled with an actuation mechanism that articulates an end effector jaw that is operable to grip a tissue. Motion of the drive link 156 causes articulation of a second of the two members. For example, motion of the drive link 156 can be used to articulate a cutter operable to cut a tissue, for example, a tissue gripped by an end effector jaw.

The actuation mechanism 140 is configured to produce substantially no movement of the drive link 156 during a first portion of a range of motion of the input link 142 and to produce substantially axial movement of the drive link 156 during a second portion of the range of motion of the input link 142. The input link 142 includes the slot 158 and the first toggle link 146 includes the follower 160 that engages the slot 158. The slot 158 includes a first segment 168 having a centerline with a substantially constant radius relative to the rotation axis 144 and a second segment 170 having a centerline with a varying radius relative to the rotation axis 144. The follower 160 engages the slot 158 along the first segment 168 during the first portion of the range of motion of the input link 142 and engages the slot 158 along the second segment 170 during the second portion of the range of motion of the input link 142. During the first portion of the range of motion of the input link 142, the substantially constant radius of the first segment 168 of the slot 158 produces no movement of the first toggle link 146, thereby producing no movement of the drive link 156. During the second portion of the range of motion of the input link 142, the varying radius of the second segment 170 of the slot 158 produces clockwise movement of the first toggle link 146 about the first pivot point 148, which produces a corresponding clockwise motion of the second toggle link 152 about the second pivot point 154, which produces an upward substantially axial movement of the drive link 156. By reversing the motion of the input link 142, an opposite downward substantially axial movement of drive link 156 occurs during the second portion of the range of motion, thereby returning the drive link 156 to its starting position.

In many embodiments, the input link 142 is coupled to the first of the two members through a mechanism that allows the first of the two members to be substantially stationary during the second portion of the range of motion of the input link 142. For example, when the input link 142 is drivingly coupled with an actuation mechanism that articulates a jaw operable to grip a tissue, a spring loaded mechanism similar to the actuation mechanism 120 described above can be used to provide for relative movement during the second portion of the range of motion of the input link 142 between the input link 142 and an output link that is drivingly coupled with the actuation mechanism that articulates a jaw operable to grip a tissue. Additional approaches for coupling the input link 142 to the first of the two members so as to allow for relative movement between the input link 142 and the first of the two members during the second portion of the range of motion of the input link 142 are described in U.S. Provisional Application No. 61/491,804, entitled "Grip Force Control in a Robotic Surgical Instrument," filed on May 31, 2011, the full disclosure of which is incorporated herein by reference.

Figure 11:
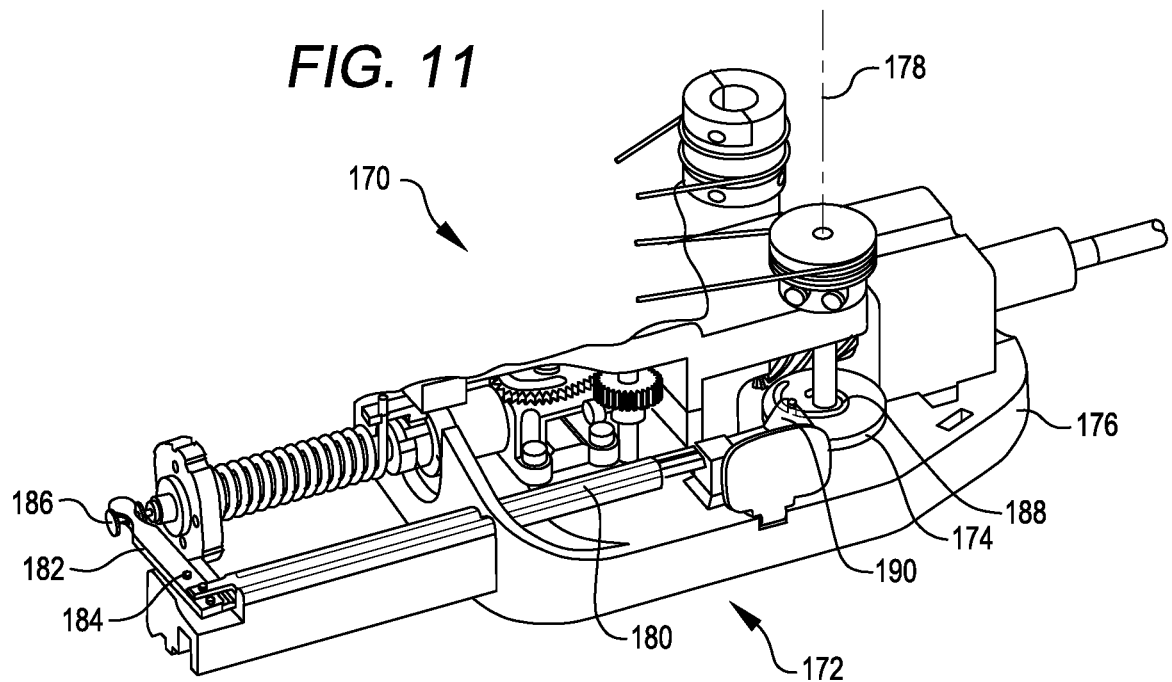
FIG. 11 is a perspective view of a proximal chassis of a surgical instrument that includes a mechanism that actuations a cutter during a second portion of a range of rotational motion of an input link, in accordance with many embodiments.

FIG. 11 shows a proximal chassis 170 of a surgical instrument that includes an actuation mechanism 172 in which a single input link 174 is used to sequentially articulate two members, in accordance with many embodiments. The actuation mechanism 122 includes the input link 174 mounted to a base 176 for rotation about a rotation axis 178, a first link 180 mounted to the base to translate in one direction relative to the base, a toggle link 182 mounted for rotation relative to the base around a pivot point 184, and a drive link 186. The input link 174 includes a slot 188 and the first link 180 includes a follower 190 that engages the slot 188. The slot 188 includes a first segment having a centerline with a substantially constant radius relative to the rotation axis 178 and a second segment having a centerline with a varying radius relative to the rotation axis 178. The follower 190 engages the slot 188 along the first segment during the first portion of the range of motion of the input link 174 and engages the slot 188 along the second segment during the second portion of the range of motion of the input link 174. During the first portion of the range of motion of the input link 174, the substantially constant radius of the first segment of the slot 188 produces no movement of the first link 180, thereby producing no movement of the drive link 186. During the second portion of the range of motion of the input link 174, the varying radius of the second segment of the slot 188 produces axial movement of the first link 180, which produces a clockwise motion of the toggle link 182 about the pivot point 184, which produces a distal substantially axial movement of the drive link 186. By reversing the motion of the input link 174, an opposite proximal substantially axial movement of drive link 186 occurs during the second portion of the range of motion, thereby returning the drive link 186 to its starting position.

As described above with regard to the input link 142 of the actuation mechanism 140, the input link 174 of the actuation mechanism 172 can be coupled to the first of the two members through a mechanism that allows the first of the two members to be substantially stationary during the second portion of the range of motion of the input link 174 using similar approaches.

Figure 12:
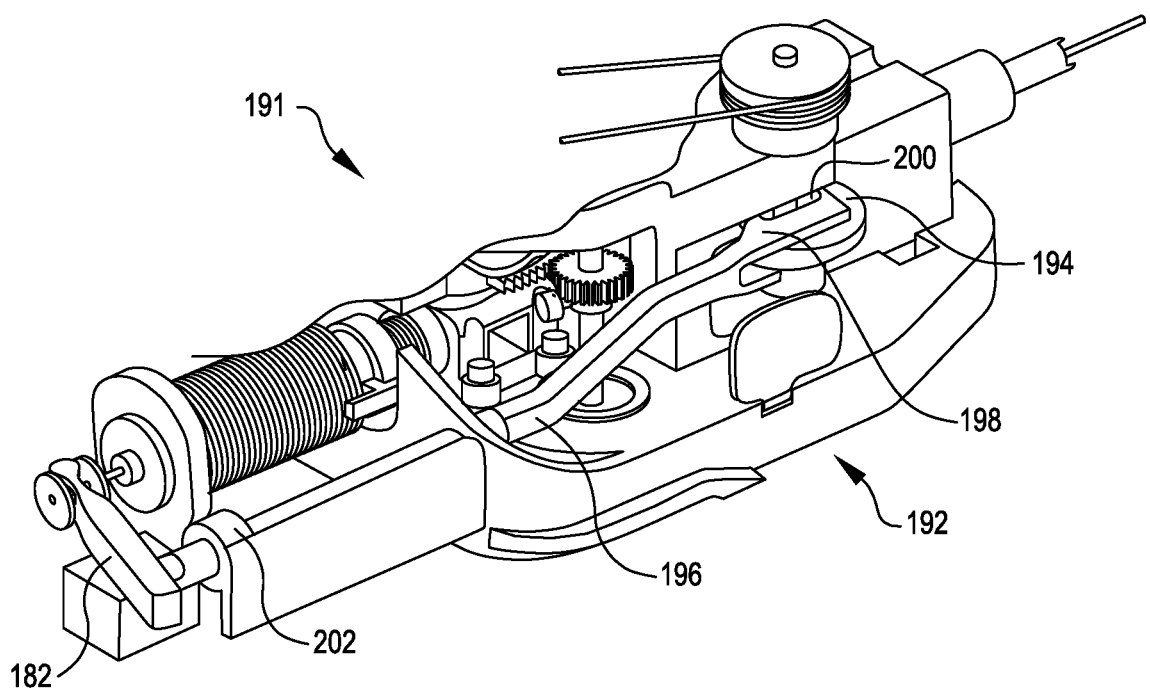
FIG. 12 is a perspective view of a proximal chassis of another surgical instrument that includes a mechanism that actuations a cutter during a second portion of a range of rotational motion of an input link, in accordance with many embodiments.

FIG. 12 shows a proximal chassis 191 of another surgical instrument that includes an actuation mechanism 192 in which a single input link 194 is used to sequentially articulate two members, in accordance with many embodiments. The actuation mechanism 192 is configured and operates similar to the actuation mechanism 172 discussed above. The actuation mechanism 192 does include some addition features. These additional features include a first link 196 that includes a double shear clevis 198 having a guide slot 200. The double shear clevis 198 provides double shear support of the follower that engages the slot in the input link 194. The guide slot 200 serves to restrain the follower end of the first link 196 against any movement of the follower end transverse to the direction in which the first link is mounted to translate relative to the base. An end restraint 202 is also provided adjacent to the connection between the first link 196 and the toggle link 182 to restrain the end of the first link against any movement transverse to the direction in which the first link is mounted to translate relative to the base.

Figure 13A:
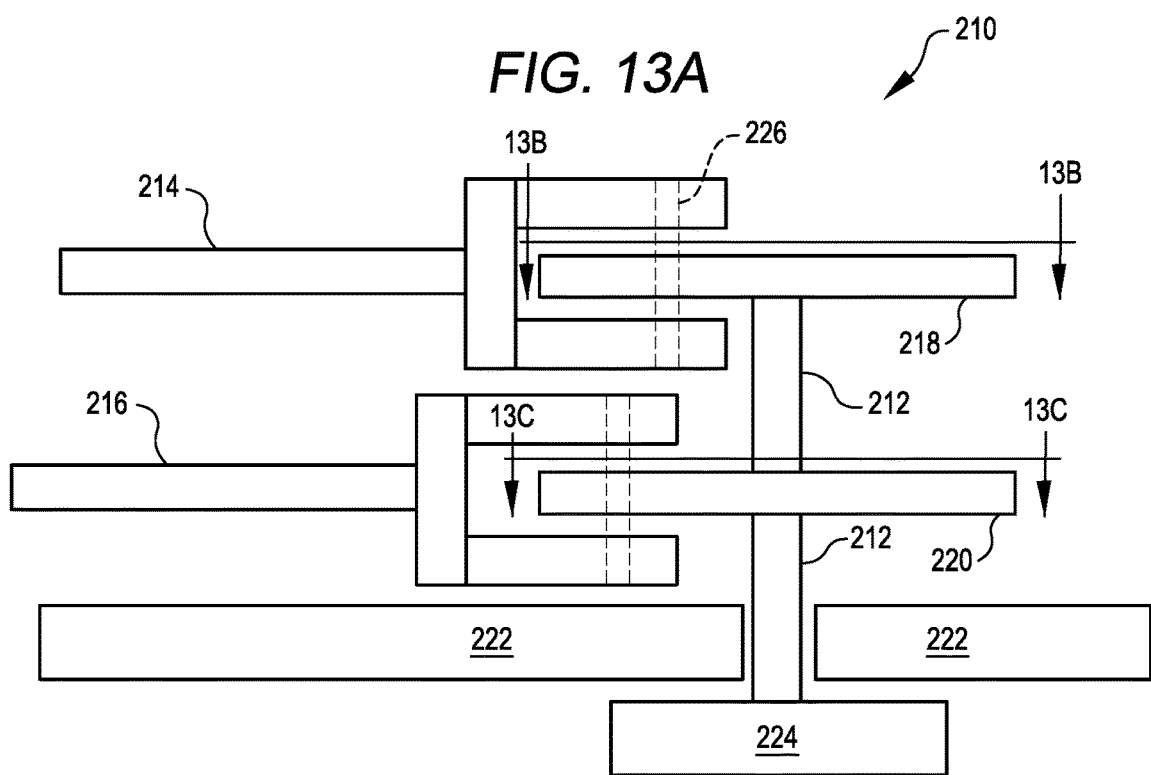
FIG. 13A schematically illustrates an actuation mechanism having two separate slotted members rotationally coupled with a common input link to drive two separate output links, in accordance with many embodiments.
Figure 13B:
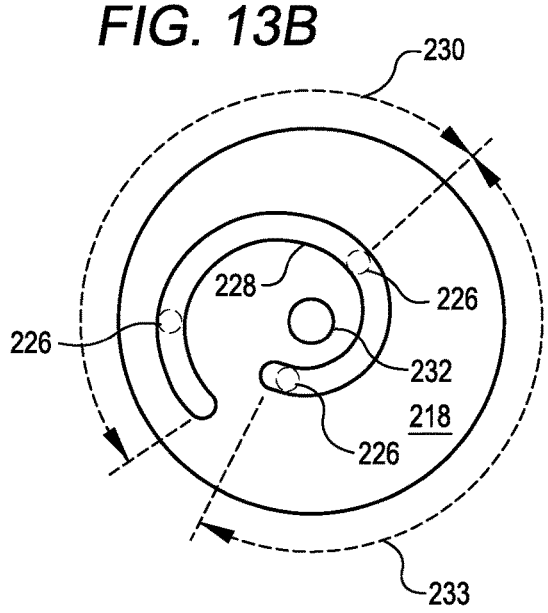
FIG. 13B schematically illustrates a first slotted member of the actuation mechanism of FIG. 13A.
Figure 13C:
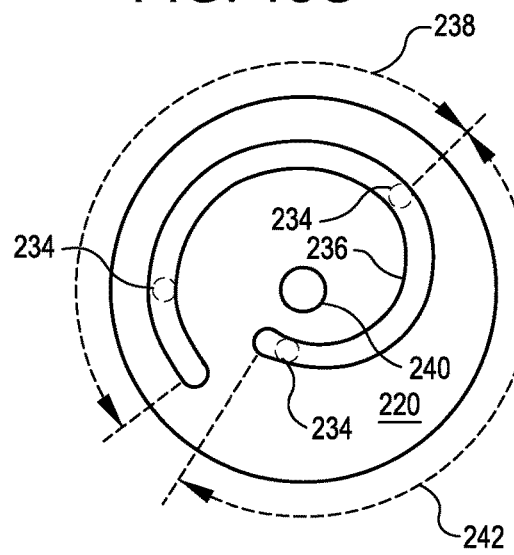
FIG. 13C schematically illustrates a second slotted member of the actuation mechanism of FIG. 13A.

FIG. 13A, FIG. 13B, and FIG. 13C schematically illustrate an actuation mechanism 210 in which a single input link is used to sequentially articulate two output links, in accordance with many embodiments. The actuation mechanism 210 includes an input link 212, a first output link 214, a second output link 216, a first slotted member 218, and a second slotted member 220.

The input link 212 is mounted for rotation relative to a base 222 (e.g., a proximal chassis of a surgical instrument as described herein). The input link 212 is attached to an input coupler 224 that is configured to interface with and be rotationally driven by an output coupler of the Patient Side Cart 22. Each of the first and second slotted members 218, 220 is attached to the input link 212 to rotate therewith.

The first output link 214 is constrained to translate along a direction of motion and includes a follower 226 that engages a slot 228 in the first slotted member 218. FIG. 13B illustrates the slot 228, which includes a first segment 230 having a varying radius relative to a rotational center 232 of the first slotted member 218, and a second segment 233 having a substantially constant radius relative to the rotational center 232. In many embodiments, the first output link 214 is constrained to translate along a line that intersects or passes relatively close to the rotational center 232 so as to substantially align the force applied to the first output link 214 by the first slotted member 218 with the direction of motion of the first output link 214. Rotation of the first slotted member 218 by the input link 212 causes translation of the first output link 214 along its direction of motion when the follower 226 is engaged by the first segment 230 of the slot 228. This translation of the first output link 214 is caused by the change in radial position between the follower 226 and the rotational center 232 when the follower 226 is engaged by the first segment 230. And rotation of the first slotted member 218 by the input link 212 produces substantially zero translation of the first output link 214 along its direction of motion when the follower 226 is engaged by the second segment 233 of the slot 228. The substantially zero translation of the first output link 214 results from the constant radial position between the follower 226 and the rotational center 232 when the follower 226 is engaged by the second segment 233.

The second output link 216 is constrained to translate along a direction of motion and includes a follower 234 that engages a slot 236 in the second slotted member 220. FIG. 13C illustrates the slot 236, which includes a first segment 238 having a substantially constant radius relative to a rotational center 240 of the second slotted member 220, and a second segment 242 having a varying radius relative to the rotational center 240. In many embodiments, the second output link 216 is constrained to translate along a line that intersects or passes relatively close to the rotational center 240 so as to substantially align the force applied to the second output link 216 by the second slotted member 220 with the direction of motion of the second output link 216. Rotation of the second slotted member 220 by the input link 212 produces substantially zero translation of the second output link 216 along its direction of motion when the follower 234 is engaged by the first segment 238 of the slot 236. The substantially zero translation of the second output link 216 results from the constant radial position between the follower 234 and the rotational center 240 when the follower 234 is engaged by the first segment 238. And rotation of the second slotted member 220 by the input link 212 causes translation of the second output link 216 along its direction of motion when the follower 234 is engaged by the second segment 242 of the slot 236. This translation of the second output link 216 is caused by the change in radial position between the follower 234 and the rotational center 240 when the follower 234 is engaged by the second segment 242.

In operation, the first output link 214 translates and the second output link 216 remains stationary during a first portion of a range of rotation of the input link 212, and the first output link 214 remains stationary and the second output link 216 translates during a second portion of a range of rotation of the input link 212. During the first portion of the range of rotation of the input link 212, the first output link follower 226 is engaged by the first segment 230 of the slot 228 in the first slotted member 218 and the second output link follower 234 is engaged by the first segment 238 of the slot 236 in the second slotted member 220. During the second portion of the range of rotation of the input link 212, the first output link follower 226 is engaged by the second segment 233 of the slot 228 in the first slotted member 218 and the second output link follower 234 is engaged by the second segment 242 of the slot 236 in the second slotted member 220.

The actuation mechanism 210 can be used to articulate an end effector jaw operable to grip tissue, such as the end effector jaw 78 described herein, and an additional end effector mechanism, such as the cutter 106 described herein. For example, the first output link 214 can be drivingly coupled with an end effector jaw operable to grip a patient tissue and the second output link 216 can be drivingly coupled with a cutter operable to cut the gripped patient tissue. In such an arrangement, rotation of the input link 212 through the first range of rotation causes articulation of the end effector jaw to grip a patient tissue along with no substantial movement of the cutter. Then, further rotation of the input link 212 through the second range of rotation causes no further articulation of the end effector jaw along with articulation of the cutter to cut the gripped tissue. Other end effector mechanisms (e.g., a mechanism for deploying staples) can also be articulated by the actuation mechanism 210. For example, the first output link 214 can be drivingly coupled with a staple deploying mechanism and the second output link 216 can be drivingly coupled with a cutter mechanism, thereby providing for a sequential deployment of staples followed by actuation of the cutter to cut the stapled tissue.

In many embodiments, the first output link 214 and/or the second output link 216 is coupled to its respective end effector mechanism by a spring loaded mechanism similar to the actuation mechanism 120 describe herein so as to control the amount of force transferred to the end effector mechanism by providing for relative movement between the respective output link and the respective end effector mechanism. Additional approaches for coupling the output links 214, 216 to a respective end effector mechanism are described in U.S. Provisional Application No. 61/491,804, entitled "Grip Force Control in a Robotic Surgical Instrument," filed on May 31, 2011, which has been incorporated by reference above.

Surgical Assembly Applications

The surgical assemblies and instruments disclosed herein can be employed in any suitable application. For example, the surgical assemblies disclosed herein can be employed in other surgical instruments, manual or powered, hand-held or robotic, directly controlled or teleoperated, for open or minimally invasive (single or multi-port) procedures. Examples of such instruments include those with distal components that receive torque actuating inputs (e.g., for grip control functions, component orientation control functions, component position functions, etc.). Illustrative non-limiting examples include teleoperated or hand-held instruments that include stapling, cutting, tissue fusing, imaging device orientation and position control, high force grasping, biopsy, and end effector and orientation control.

Methods for Articulating Two Members with a Single Drive Input

FIG. 14 illustrates acts of a method 250 for articulating an end effector of a surgical assembly, in accordance with many embodiments. The method 250 can be practiced, for example, with the surgical assemblies and/or instruments disclosed herein.

The method 250 includes moving an input link relative to a base through a range of motion (act 252), articulating a first member of the end effector within a first portion of the range of motion (act 254), and articulating a second member of the end effector within a second portion of the range of motion (act 256). The first and second members are different. And the articulation of the first member and the articulation of the second member are primarily independent.

In many embodiments, the end effector is configured to treat a tissue. For example, the articulated first member of the end effector can include a jaw configured to grip a tissue, and the articulated second member of the end effector can include a cutter configured to cut the tissue. The jaw can have a first articulation range configured to grip the tissue and the cutter can have a second articulation range configured to cut the tissue. Movement of the input link can actuate the jaw throughout the first articulation range primarily within the first portion of the range of motion, and can actuate the cutter throughout the second articulation range within the second portion of the range of motion. In many embodiments, the first and second portions of the range of motion are separate so as to facilitate independently gripping the tissue and cutting the gripped tissue.

Any other suitable combination of end effector articulated members can be used as the first and second members. For example, the articulated first member can include a mechanism for deploying staples into a tissue, and the articulated second member can include a cutter for cutting the stapled tissue. As another example, the articulated first member can include a jaw operable to grip a tissue, and the articulated second member can include a mechanism for deploying staples into the gripped tissue.

FIG. 15 illustrates acts of a method 260 of treating tissue, in accordance with many embodiments. The method 260 can be practiced, for example, with the surgical assemblies and/or instruments disclosed herein.

The method 260 includes moving an input link relative to a base through a range of motion (act 262), articulating a jaw within a first portion of the range of motion so as to grasp the tissue (act 264), and articulating a cutter within a second portion of the range of motion, the articulating of the jaw and the cutter being primarily independent (act 266).

In many embodiments of the method 260, the articulation of the jaw includes inhibiting relative movement between the input link and an output link during the first portion of the range of motion with a spring coupled with the input link and the output link, the output link being drivingly coupled with the jaw. The articulation of the cutter can include deflecting the spring to at least partially decouple motion of the output link from the input link during the second portion of the range of motion. Any suitable type of spring can be used (e.g., an extension spring, a torsion spring). Any suitable type of motion of the input link relative to the base can be used to induce the articulation of the jaw and cutter (e.g., translation of the input link relative to the base, rotation of the input link relative to the base).

The cutter can be articulated by using a cam surface that is drivingly coupled with the input link and a follower that engages the cam surface and is drivingly coupled with the cutter. For example, the method 260 can include rotating a member having a slot in response to rotation of the input link, and engaging the slot with a follower that is drivingly coupled with the cutter. The slotted member can be rotated about an axis of rotation relative to the base. The slot can include a first segment having a centerline with a constant radius relative to the axis of rotation and a second segment having a centerline with a varying radius relative to the axis of rotation. The follower can engage the first segment during the first portion of the range of motion. And the follower can engage the second segment during the second portion of the range of motion.

Two or more slotted members can be used to drive a corresponding two or more end effector mechanisms. For example, the method 260 can include rotating a first member having a first slot in response to rotation of the input link, engaging the first slot with a first follower that is drivingly coupled with the jaw, rotating a second member having a second slot in response to rotation of the input link, and engaging the second slot with a second follower that is drivingly coupled with the cutter.

Method Applications

The methods disclosed herein can be employed in any suitable application. For example, the methods disclosed herein can be employed in surgical instruments, manual or powered, hand-held or robotic, directly controlled or teleoperated, for open or minimally invasive (single or multiport) procedures. Examples of such instruments include those with distal components that receive actuating inputs (e.g., for grip control functions, component orientation control functions, component position functions, etc.). Illustrative non-limiting examples include teleoperated or handheld instruments that include stapling, cutting, tissue fusing, imaging device orientation and position control, high force grasping, biopsy, and end effector and orientation control.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The term "force" is to be construed as encompassing both force and torque (especially in the context of the following claims), unless otherwise indicated herein or clearly contradicted by context. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A medical device, comprising:
a base;
an input link mounted to the base, the input link being rotatable around an input link rotation axis relative to the base;

a first slotted member attached to the input link to rotate with the input link around the input link rotation axis, the first slotted member comprising a first slot having a first shape;
a second slotted member attached to the input link to rotate with the input link around the input link rotation axis, the second slotted member comprising a second slot having a second shape different from the first shape;
a first output link drivingly engaged with the first slot; and
a second output link drivingly engaged with the second slot.

2. The medical device of claim 1, wherein:
the medical device further comprises an input coupler attached to the input link; and
the input coupler is configured to be rotationally driven by an output coupler of a surgical instrument manipulator.

3. The medical device of claim 1, wherein:
the first output link is constrained to translate along a first output link direction of motion relative to the base; and
the first output link direction of motion intersects the input link rotation axis.

4. The medical device of claim 1, wherein:
the first slotted member comprises a first rotational center at which the first slotted member is attached to the input link;
the second slotted member comprises a second rotational center at which the second slotted member is attached to the input link;
within a first range of rotational motion of the input link, the first slot comprises a varying radius relative to the first rotational center, and the second slot comprises a constant radius relative to the second rotational center;
within a second range of rotational motion of the input link, the first slot comprises a constant radius relative to the first rotational center, and the second slot comprises a varying radius relative to the second rotational center; and
the second range of rotational motion is different from the first range of rotational motion.

5. The medical device of claim 4, wherein:
the medical device further comprises an input coupler attached to rotationally drive the input link; and
the input coupler is configured to be rotationally driven by an output coupler of a surgical instrument manipulator.

6. The medical device of claim 1, wherein:
on a condition the input link moves through a first range of rotation, the first output link translates relative to the base, and the second output link remains stationary relative to the base; and
on a condition the input link moves through a second range of rotation different from the first range of rotation, the second output link translates relative to the base, and the first output link remains stationary relative to the base.

7. The medical device of claim 6, wherein:
the medical device further comprises an input coupler attached to rotationally drive the input link; and
the input coupler is configured to be rotationally driven by an output coupler of a surgical instrument manipulator.

8. The medical device of claim 6, wherein:
the medical device further comprises an end effector, and the end effector comprises a jaw and an additional mechanism;
the first output link is drivingly coupled with the jaw; and
the second output link is drivingly coupled with the additional mechanism.

9. The medical device of claim 8, wherein:
the jaw is operable to grip tissue; and
the additional mechanism is a cutter operable to cut tissue gripped by the jaw.

10. A medical device, comprising:
a base;
an input link mounted to the base and rotatable around an input link rotation axis relative to the base;
a drive member attached to the input link to rotate with the input link relative to the base; and
an output link drivingly engaged with the drive member such that the output link translates relative to the base through a first range of rotation of the input link, and such that the output link remains stationary relative to the base through a second range of rotation of the input link different from the first range of rotation.

11. The medical device of claim 10, wherein:
the medical device further comprises an input coupler attached to the input link; and
the input link is configured to be rotationally driven by an output coupler of a robotic surgical instrument manipulator.

12. The medical device of claim 11, wherein the output link translates relative to the base in an output link direction of motion that intersects the input link rotation axis.

13. The medical device of claim 10, wherein:
the medical device comprises an end effector;
the end effector comprises a jaw; and
the output link is drivingly coupled with the jaw.

14. The medical device of claim 10, wherein:
the medical device comprises a staple deploying mechanism; and
the output link is drivingly coupled with the staple deploying mechanism.

15. The medical device of claim 10, wherein:
the medical device comprises an end effector orientation control mechanism; and
the output link is drivingly coupled with the end effector orientation control mechanism.

16. A medical device comprising:
an input link, a first slotted member coupled to be driven by the input link, a second slotted member coupled to be driven by the input link, a first output link, and a second output link;
the first slotted member comprising a first slot,
the first slot comprising a first segment and a second segment,
the first segment of the first slot having a first shape, and
the second segment of the first slot having a second shape different from the first shape of the first segment of the first slot;
the second slotted member comprising a second slot,
the second slot comprising a first segment and a second segment,
the first segment of the second slot having a first shape,
the second segment of the second slot having a second shape,
the first shape of the first segment of the second slot being different from the first shape of the first segment of the first slot, and
the second shape of the second segment of the second slot being different from the second shape of the second segment of the first slot;
the first output link being drivingly engaged with the first slot of the first slotted member; and
the second output link being drivingly engaged with the second slot of the second slotted member.

17. The medical device of claim 16, wherein:

an axis of rotation is defined for the input link, and the input link rotates about the axis of rotation in a first range of rotation and a second range of rotation different from the first range of rotation;

the first slotted member comprises a first center of rotation and is coupled to the input link at the first center of rotation;

the second slotted member comprises a second center of rotation and is coupled to the input link at the second center of rotation;

during rotation of the input link in the first range of rotation, the first output link is drivingly engaged with the first segment of the first slot, and the second output link is drivingly engaged with the first segment of the second slot; and during rotation of the input link in the second range of rotation, the first output link is drivingly engaged with the second segment of the first slot, and the second output link is drivingly engaged with the second segment of the second slot.

18. The medical device of claim 17, wherein:

the first shape of the first segment of the first slot is a varying radius relative to the first center of rotation of the first slotted member;

the second shape of the second segment of the first slot is a constant radius relative to the first center of rotation of the first slotted member;

the first shape of the first segment of the second slot is a constant radius relative to the second center of rotation of the second slotted member; and the second shape of the second segment of the second slot is a varying radius relative to the second center of rotation of the second slotted member.

19. A medical device comprising:

an input link, a first slotted member coupled to be rotated by the input link, a second slotted member coupled to be rotated by the input link, a first output link, and a second output link;

the first slotted member comprising a first slot, and the first slot comprising a varying radius relative to a center of rotation of the first slotted member;

the second slotted member comprising a second slot, and the second slot comprising a varying radius relative to a center of rotation of the second slotted member;

the first output link drivingly being engaged with the first slot of the first slotted member; and the second output link being drivingly engaged with the second slot of the second slotted member.

20. The medical device of claim 19, wherein:

the input link moves in a first range of motion and a second range of motion different from the first range of motion;

the first slot comprises a constant radius relative to the center of rotation of the first slotted member;

the second slot comprises a constant radius relative to the center of rotation of the second slotted member;

the first range of motion of the input link corresponds to the varying radius of the first slot and the constant radius of the second slot; and the second range of motion of the input link corresponds to the constant radius of the first slot and the varying radius of the second slot.

* * * * *